United States Patent
Tran et al.

(10) Patent No.: US 8,068,931 B2
(45) Date of Patent: Nov. 29, 2011

(54) SYSTEMS AND METHODS FOR MONITORING PILL TAKING

(76) Inventors: Alan An Thuan Tran, San Jose, CA (US); Bao Q. Tran, San Jose, CA (US)

( * ) Notice: Subject to any disclaimer, the term of this patent is extended or adjusted under 35 U.S.C. 154(b) by 1211 days.

(21) Appl. No.: 11/588,197

(22) Filed: Oct. 24, 2006

(65) Prior Publication Data
US 2008/0105588 A1 May 8, 2008

(51) Int. Cl.
*G06F 17/00* (2006.01)
(52) U.S. Cl. ............ 700/236; 221/2; 221/4; 221/7; 206/534
(58) Field of Classification Search .......... 700/231–244; 221/1–312 C, 2, 4, 7; 206/534
See application file for complete search history.

(56) References Cited

U.S. PATENT DOCUMENTS

| | | | |
|---|---|---|---|
| 4,572,403 A | | 2/1986 | Benaroya |
| 4,573,606 A | | 3/1986 | Lewis et al. |
| 4,674,651 A | | 6/1987 | Scidmore et al. |
| 4,838,453 A | | 6/1989 | Luckstead |
| 4,971,221 A | * | 11/1990 | Urquhart et al. ............ 221/2 |
| 5,044,516 A | | 9/1991 | Hoar |
| 5,088,056 A | * | 2/1992 | McIntosh et al. ........... 702/177 |
| 5,176,285 A | | 1/1993 | Shaw |
| 5,200,891 A | * | 4/1993 | Kehr et al. ................. 221/2 |
| 5,412,372 A | * | 5/1995 | Parkhurst et al. .......... 340/568.1 |
| 6,510,962 B1 | | 1/2003 | Lim |
| 7,088,233 B2 | * | 8/2006 | Menard ...................... 340/539.1 |
| 7,233,228 B2 | * | 6/2007 | Lintell ........................ 340/309.7 |
| 7,424,888 B2 | * | 9/2008 | Harvey et al. ............. 128/203.15 |
| 2006/0139150 A1 | * | 6/2006 | Brue .......................... 340/309.16 |

* cited by examiner

*Primary Examiner* — Michael K Collins
(74) *Attorney, Agent, or Firm* — Tran & Associates

(57) ABSTRACT

Systems and methods are disclosed for dispensing one or more pills from a pill box by applying power when the one or more pills are poured from the pill box; identifying an opened compartment and an opening time; and recording the opened compartment and the opening time.

19 Claims, 6 Drawing Sheets apply power when the one or more pills are poured from the pill box (100)

identify an opened compartment and an opening time (102)

record the opened compartment and the opening time (104)

check the opening time against one or more medication constraints and if so, generate an alarm if the medication constraint is violated (106)

check for multiple compartment openings during one medication dispensing event and if so, generate an alarm (108)

wirelessly transmit the recorded opened compartment and opening time to a computer (110)

allow one or more authorized persons to review the medication dispensing (112)

request a medication refill if needed (114)

FIG. 5

| |
|---|
| optionally ask if patient would like information about medication and if so display a summary of the medication, requirements prior to taking medication, and potential side effects to be aware of(200) |
| identify an opened compartment and an opening time (202) |
| record the opened compartment and the opening time (204) |
| check the opening time against one or more medication constraints and if so, generate an alarm if the medication constraint is violated (206) |
| check for multiple compartment openings during one medication dispensing event and if so, generate an alarm (208) |
| optionally query other devices to collect information on patient (210) |
| optionally display one or more predesigned questions about the user's health and collect answer(s) from the question(s) (212) |
| wirelessly transmit the recorded opened compartment and opening time and other collected patient data to a computer (214) |
| allow one or more authorized persons to review the medication compliance information and collected patient data (216) |
| request a medication refill if needed (218) |

FIG. 6

SYSTEMS AND METHODS FOR MONITORING PILL TAKING

BACKGROUND

This invention relates to pill dispensers.

The usage of pills to regain and maintain health has increased with the advancement of medical science. It is not unusual for a person to take more than one type of pill, each type in a different amount, at regular times each day. The task of correctly taking several different types of pills pose a challenge to many individuals, especially the elderly, the mentally infirm, and the obtunded who are more susceptible to memory problems. The improper taking of pills may be detrimental to health, and many emergency hospital admissions are attributable to improper observance of pill prescriptions.

The need for a device that will automatically dispense the proper pill(s) in the proper amount(s) at the proper time(s) each day and alert the user of the device to take the dispensed pill(s) is evident by the numerous devices described in the prior art. However, there are problems with the devices described in the prior art. For example, U.S. Pat. No. 4,573,606 to Lewis et al. (1986), U.S. Pat. No. 4,674,651 to Scidmore et al. (1987), U.S. Pat. No. 4,838,453 to Luckstead (1989), and U.S. Pat. No. 5,044,516 to Hoar (1991) describe automatic pill dispensers which have pill-storage wheels that are rotated constantly by electric clock motors. The constantly rotating pill-storage wheels of these devices successively move each pill-storage compartment of the wheel into a temporary alignment with a pill discharge outlet at a cyclical and fixed time interval. When a pill-storage compartment is in alignment with the pill discharge outlet, any pill stored in the compartment will fall by gravity through the outlet into a pill receptacle. The length of the fixed time interval of these devices cannot be changed without changing the gear drive ratio of the gear system driving the pill-storage wheel. Discharging pills at fixed time intervals makes these devices inefficient and difficult to use. For example, if one of these devices constantly rotates three pill-storage compartments past its pill discharge outlet in a 24-hour period, but only one pill is needed each day, then only one pill-storage compartment is used and two are kept empty each 24-hour day. In this case, two out of three pill-storage compartments have no use. In addition, during the process of loading pills into the pill storage wheel, specific compartments must be kept empty; this makes the loading procedure more complicated and susceptible to error.

Another problem with all of these devices is the possibility of an overdose of dispensed pills. This may result when a device dispenses pills into the pill receptacle, but the person taking the dispensed pills for some reason did not respond to the alert signal or just turned off the alert signal without taking the pills. If the dispensed pills are not removed from the pill receptacle and more pills are discharged into the receptacle, overdosing with harmful consequences may occur if the pill taker consumes all of the pills accumulated in the pill receptacle all at once.

Benaroya in U.S. Pat. No. 4,572,403 (1983), and Shaw in U.S. Pat. No. 5,176,285 (1993) attempt to overcome these deficiencies. The devices of Benaroya and Shaw include pill-storage wheels which rotate into position for discharging pills only when the pills are to be dispensed. A pill is not released from Shaw's pill-storage wheel unless a motorized mechanism is actuated to remove the pill, making an accumulation of discharged pills less likely. However, Shaw's device is complicated, difficult to load with pills and use, and uses motors and controls which are neither simple nor economical. Pills to be dispensed by Benoroya's device are not automatically discharged by gravity into a fixed or removable pill receptacle. The pills stay in the pill-storage wheel until the user tilts or turns the device upside down to dump out the pills. While this feature makes overdosing from an accumulation of discharged pills unlikely, the need to manipulate the device by tilting or turning it upside down and catching the pills before they fall on the floor makes its operation ackward and clumsy.

U.S. Pat. No. 6,510,962 describes a device that can be loaded with appropriate pills and programmed to automatically dispense the proper amount(s) and proper type(s) of pill(s) at the proper time(s) each day. The device includes a system for alerting the pill taker that pills have been dispensed, a system for providing voice messages to coach the pill taker to use the device and consume the pills, and a system for alerting an off-site caregiver when the pill taker has not responded as required or when there is a problem with the operation of the device.

U.S. Pat. No. 6,449,218 describes an electronic device for holding medicines, typically pills, to be taken at different times and to remind the user to take particular pills at specific times. A first container has a plurality of pill holding compartments, with a hinged lid closing each compartment. A second container, which is releasably fastenable to the first compartment, contains a microprocessor, an alarm, a display and buttons for controlling the microprocessor to display different information. The display can be set to show the time, times for taking pills from different compartments, whether pills have been taken on time, if a pill has been missed or skipped, when the last pill has been taken, etc. When a time set for taking a pill arrives, an alarm, typically a light and/or sound alarm, alerts the user as to the compartment holding the pill to be taken. A pill splitter is further provided that can be releasably fastened to one of the compartments and provides quick, accurate and safe splitting of pills so that halves may be placed in the compartments to be taken as indicated by the alarm system.

SUMMARY

In one aspect, a method for dispensing one or more pills from a pill box includes applying power when the one or more pills are poured from the pill box; identifying an opened compartment and an opening time; and recording the opened compartment and the opening time.

Implementations of the above method can include one or more of the following. The system can check the opening time against one or more medication constraints. The medical constraint includes taking medication on a full stomach, a non-empty stomach or taking medication on an empty stomach. The system can generate an alarm if medication is taken without meeting the appropriate food restriction. For example, if the medication is taken around normal lunch time when the medication should have been taken on an empty stomach, the system provides a warning and reports the event. The system can also check for multiple compartment openings during one medication dispensing event and appropriate alarm(s) can be generated if there is a compliance issue. The system can wirelessly transmit the recorded opened compartment and opening time to a computer such as a patient computer, a cell phone, a remote server through the patient computer over the Internet, or a remote server using Bluetooth and cellular channel. One or more authorized persons can review the medication dispensing. The system can also automatically request a medication refill from a pharmacy or from a doctor, for example.

In another aspect, a medication pill box includes a processor to detect one or more compartment openings for a pill box; a power source; and a pill dispensing sensor coupled to the power source and the processor, the pill dispensing sensor applying power to the processor when one or more pills are poured from the pill box.

Implementations of the above method can include one or more of the following. The pill box has one or more switches each coupled to a pill box compartment door to detect a compartment door opening. The switch can be a first electrically conductive portion on the compartment door adapted to contact a second electrically conductive portion on a pill box wall adapted to contact the door. The processor can check a door opening time against one or more medication constraints. The medical constraint can include taking medication on one of: a full stomach, a non-empty stomach and an empty stomach. The processor can also check for multiple compartment openings during one medication dispensing event. A wireless transmitter can send the recorded opened compartment and opening time to a computer. The computer allows one or more authorized persons to review the medication dispensing. The system can also automatically request a medication refill when the medication is almost completely dispensed. The tilt sensor such as a pendulum, an accelerometer, or a magnetic sensor can be used. The pill dispensing sensor can be a door open switch, a door closed switch, a motion sensor, a pendulum, an accelerometer, or a magnetic sensor. The system provides a built-in secure compartment for storing the pills. The system also assists users, especially those suffering from senility or deterioration of mental function, in complying with their prescriptions. The system avoids the situation where users may simply deactivate the pill alert signal as they would do when turning off an alarm clock, and forget to take the dispensed pills. The system provides special instructions that the pill taker must follow in consuming the dispensed pills, such as taking the dispensed pills with plenty of liquids, or food, and the pill taker may forget these instructions. The system automatically determines when to refill the dispenser with pills. The system can automatically request a refill from a doctor and forward the refill prescription to a pharmacy for filling. Patient safety is enhanced while the cost of emergency treatment due to non-compliance is reduced. Further, the system's wireless monitoring of drug compliance is cost-effective and convenient to the patient.

BRIEF DESCRIPTION OF THE DRAWINGS

FIG. 5 shows an exemplary method for dispensing one or more pills from the pill box and collecting medication compliance information.

FIG. 6 shows an exemplary method for dispensing pills/compliance monitoring and collecting patient data as well as providing educational information to the patient regarding the treatment using the pill box.

DESCRIPTION

Figure 1:
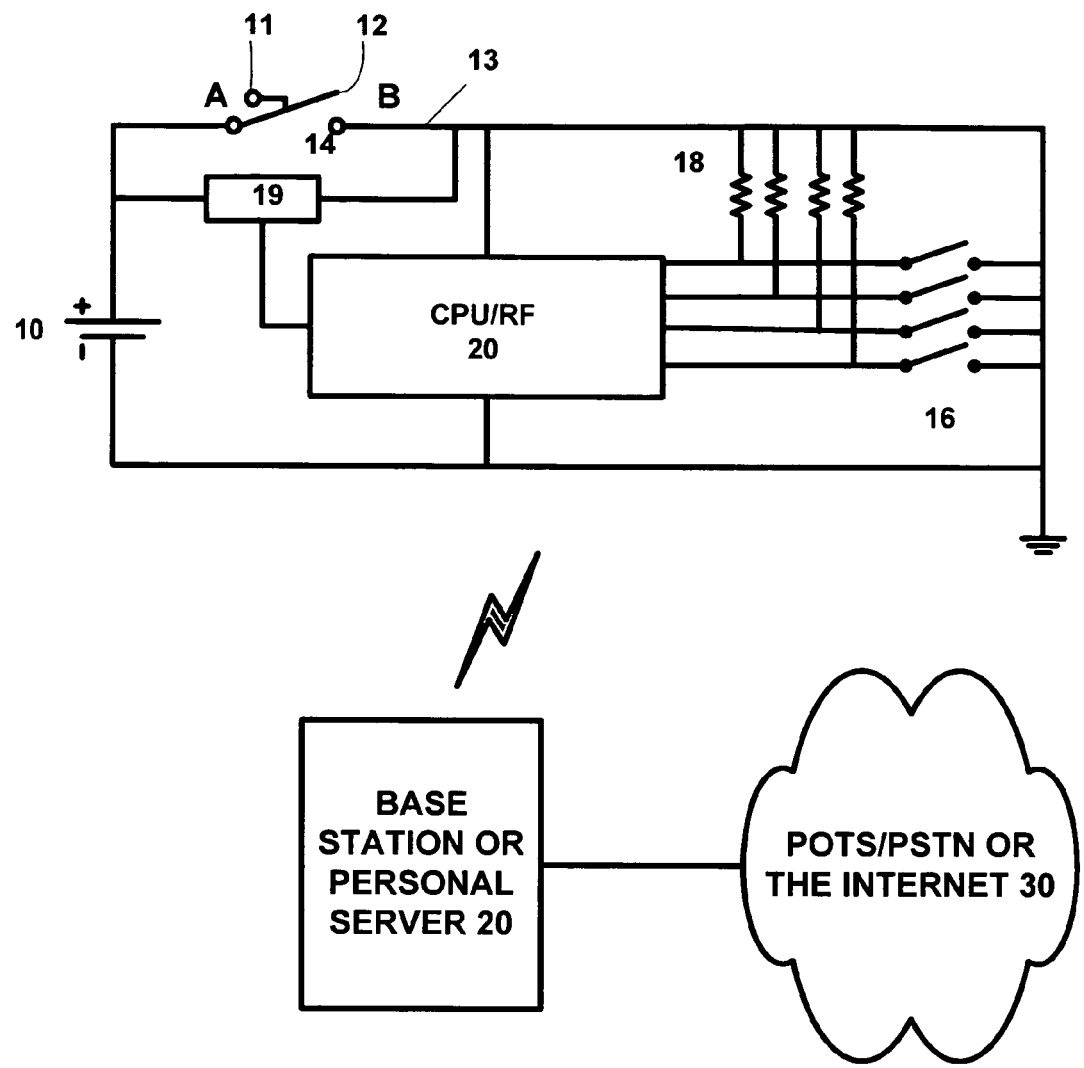
FIG. 1 shows an exemplary system that tracks medication taken by a patient.
Figure 3:
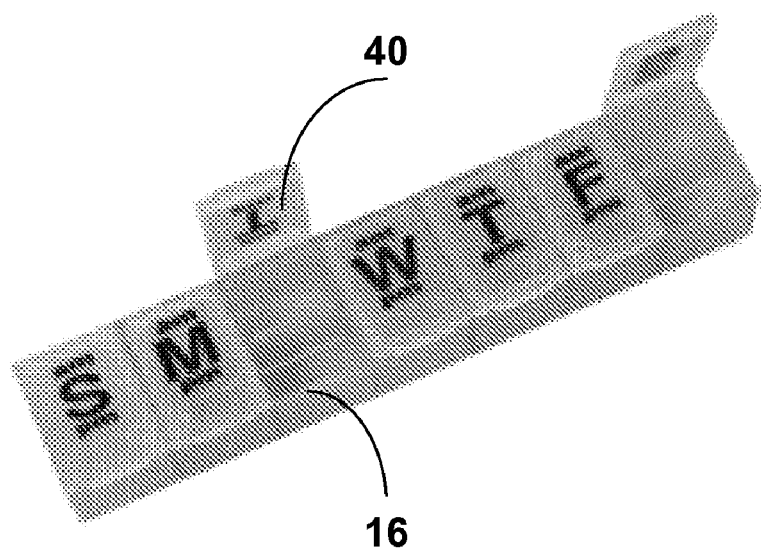
FIG. 3 shows an exemplary pill box.

FIG. 1 shows an exemplary system that tracks medication taken by a patient. In this system, a power source 10 such as a battery provides power for a pill box 44 (as shown in FIG. 3).

A pill pouring detector is used to connect the power terminal of the power source 10 to a control electronic 20 when pills are poured from the pill box 44 so that the patient can take the medication.

In one embodiment, the pill pouring detector is a tilt-sensor. The tilt-sensor can include a pendulum 12 that contacts an electrode 14 when the pills are poured from its respective compartment. A wire 11 connects the pendulum 12 to the power source 10 at terminal A, while a wire 13 connects the electrode 14 to the control electronic 20 at terminal B.

The pendulum 12 can be connected to an optional spring (not shown) to enable the pendulum 12 to contact the electrode 14 quickly. In one embodiment, one end of the spring is attached to the pill box and the other end attached to the top of the pendulum 12. The spring assists the pendulum to touch the electrode 14, thereby forming a conductive circuit for powering the electronic 20. The pendulum 12 can also be connected to an optional return spring (not shown) to enable the pendulum 12 to separate quickly.

The electrode 14 can also have an optional magnet (not shown) to attract the pendulum 12. In other embodiments, an accelerometer can be used to sense motion, or a magnet sensor can be used to detect the pill-pouring act by the patient. In yet other embodiments, a photo-detector or a camera can be positioned underneath the pill box to sense the presence or absence of pill(s) after the door is opened, for example. Other approaches can be used to detect pill pouring as well.

The control electronic 20 can be an integrated processor and radio system-on-a-chip. In one embodiment, the control electronic 20 can be a mesh network system such as ZigBee system, for example. Suitable control electronic 20 can include one chip solutions from Freescale and Texas Instruments/ChipCon, among others. The control electronic 20 has integrated mesh-network wireless transceivers, in this case ZigBee transceivers whose network features are described in more details in FIG. 2. The processor can maintain clock data using interrupt handling, or alternatively a real-time clock chip can be used to provide time of day information with precision.

In one implementation, the doors and corresponding door tabs that keep the door secured when closed are made of a conductive material such as silver or conductive plastics. When closed, the door and the door tab are electrically shorted together and thus form a circuit. When opened, the door and the door tab are electrically isolated, and the closing or opening of each door can be determined by sampling the current or voltage present on each door. The data input and output pins of the processor can be connected to door opening detection switches 16 using suitable pull-up resistors 18. Alternatively, pull-down resistors can be used to detect door openings/closings. The door opening/closing sensor is one type of pill dispensing sensor, and other sensors can include a motion sensor (such as PIR sensor), a pendulum, an accelerometer, or a magnetic sensor.

Optionally, a power switch 19 can be provided to allow the control electronic 20 sufficient time to complete its operation before releasing power in case the pendulum 12 separates from the electrode 14 before the control electronic 20 is ready. When power is initially applied by the pendulum 12, the control electronic 20 turns on the switch 19 to assure that power will be available as long as needed. When the control electronic 20 is done, it disables the power switch 19 to cut off power. The power switch 19 can be an electromechanical relay or a power transistor or any other suitable switches. The use of the pendulum 12 thus conserves battery energy and the use of the power switch 19 enables an orderly shut-down by the control electronic 20.

The control electronics 20 communicate wirelessly with a computer 20 which is connected to a wide area network 30 such as the Internet. The computer 20 can be a home server which authorized persons can log-in to monitor drug usage by the patient. Alternatively, the computer 20 can transfer data over the WAN 30 to a remote server which centralizes data from the patient for one or more groups to review.

Figure 2:
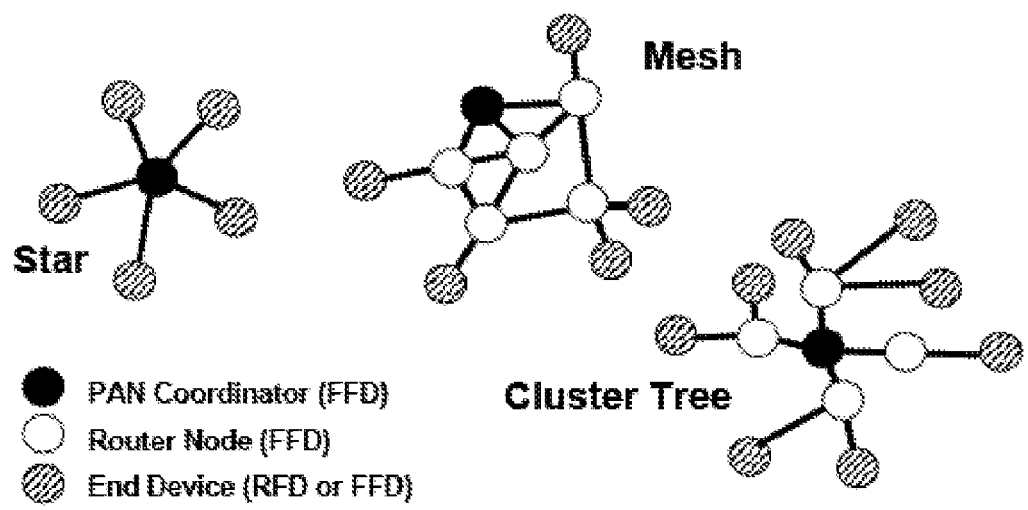
FIG. 2 shows an exemplary mesh network for data transmission by the system of FIG. 1.

FIG. 2 shows an exemplary mesh network for medication compliance data transmission by the system of FIG. 1. In one embodiment, the mesh network is an IEEE 802.15.4 (ZigBee) network. IEEE 802.15.4 defines two device types; the reduced function device (RFD) and the full function device (FFD). In ZigBee these are referred to as the ZigBee Physical Device types. In a ZigBee network a node can have three roles: ZigBee Coordinator, ZigBee Router, and ZigBee End Device. These are the ZigBee Logical Device types. The main responsibility of a ZigBee Coordinator is to establish a network and to define its main parameters (e.g. choosing a radio-frequency channel and defining a unique network identifier). One can extend the communication range of a network by using ZigBee Routers. These can act as relays between devices that are too far apart to communicate directly. ZigBee End Devices do not participate in routing. An FFD can talk to RFDs or other FFDs, while an RFD can talk only to an FFD. An RFD is intended for applications that are extremely simple, such as a light switch or a passive infrared sensor; they do not have the need to send large amounts of data and may only associate with a single FFD at a time. Consequently, the RFD can be implemented using minimal resources and memory capacity and have lower cost than an FFD. An FFD can be used to implement all three ZigBee Logical Device types, while an RFD can take the role as an End Device. In other embodiments, Bluetooth transmitters, cellular transmitters, WiFi transmitters, or WiMax transmitters can be used.

FIG. 3 shows an exemplary pill box. In this embodiment, the pill box has a seven-day planners with removable dividers that allow for 1 or 2 compartments for storing medicine. The pill box enables the patient to keep all of your medicines organized by day and time of day (AM/PM). The top of each lid has the first letter of each day of the week imprinted on it in very large black letters. In addition each letter can be stamped out in Braille. The pill box 50 has a door 40 with a conductive tab that acts as a switch 16. Upon door closure, the switch 16 is closed and upon door opening, the switch 16 is in an open state to indicate to the control electronic 20 that the door is in an open state or a closed state. The switch 16 can be made of a conductive elastomeric material or a silver ink or any other suitable conductor as long as the material can handle repetitive door openings and closings.

Figure 4A:
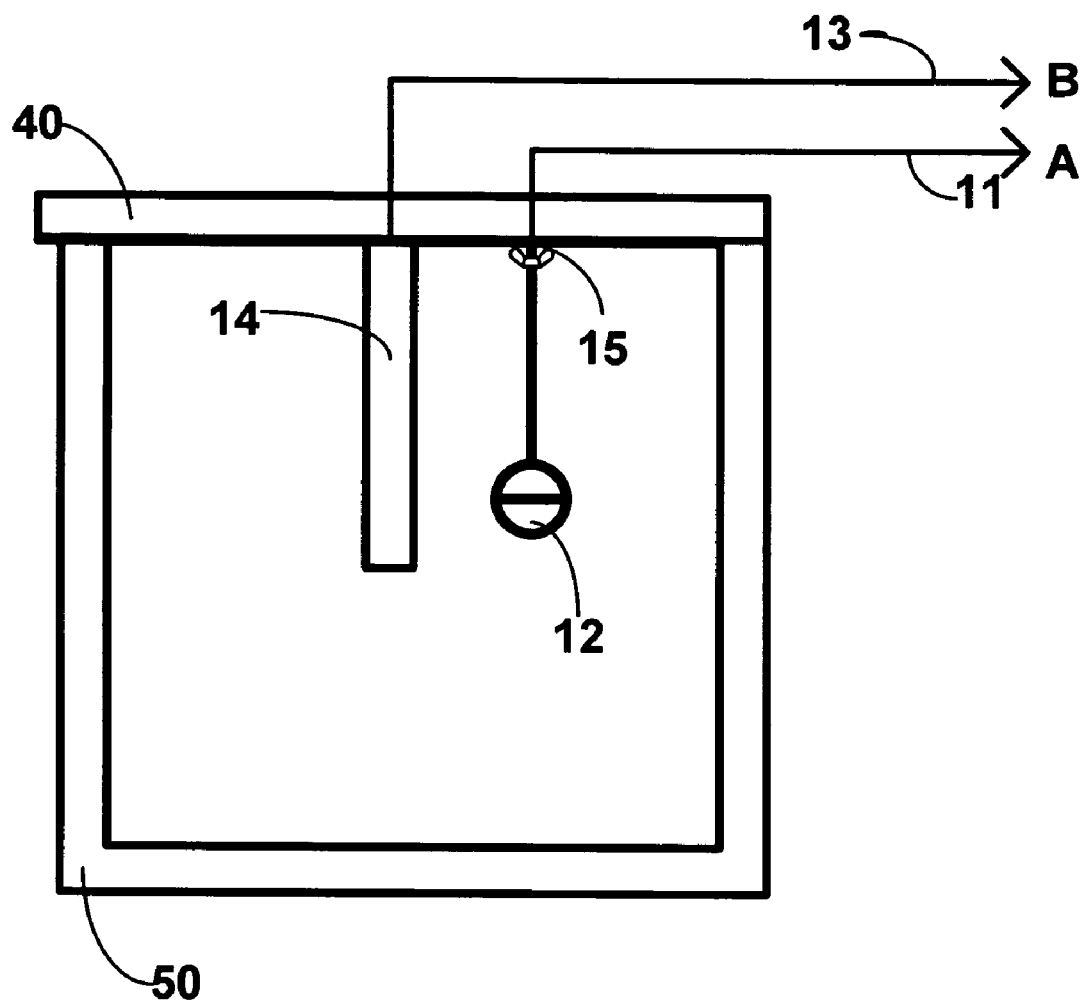
FIGS. 4A-4B show exemplary closed and open states for a pill-dispensing detector in the pill box of FIG. 3.
Figure 4B:
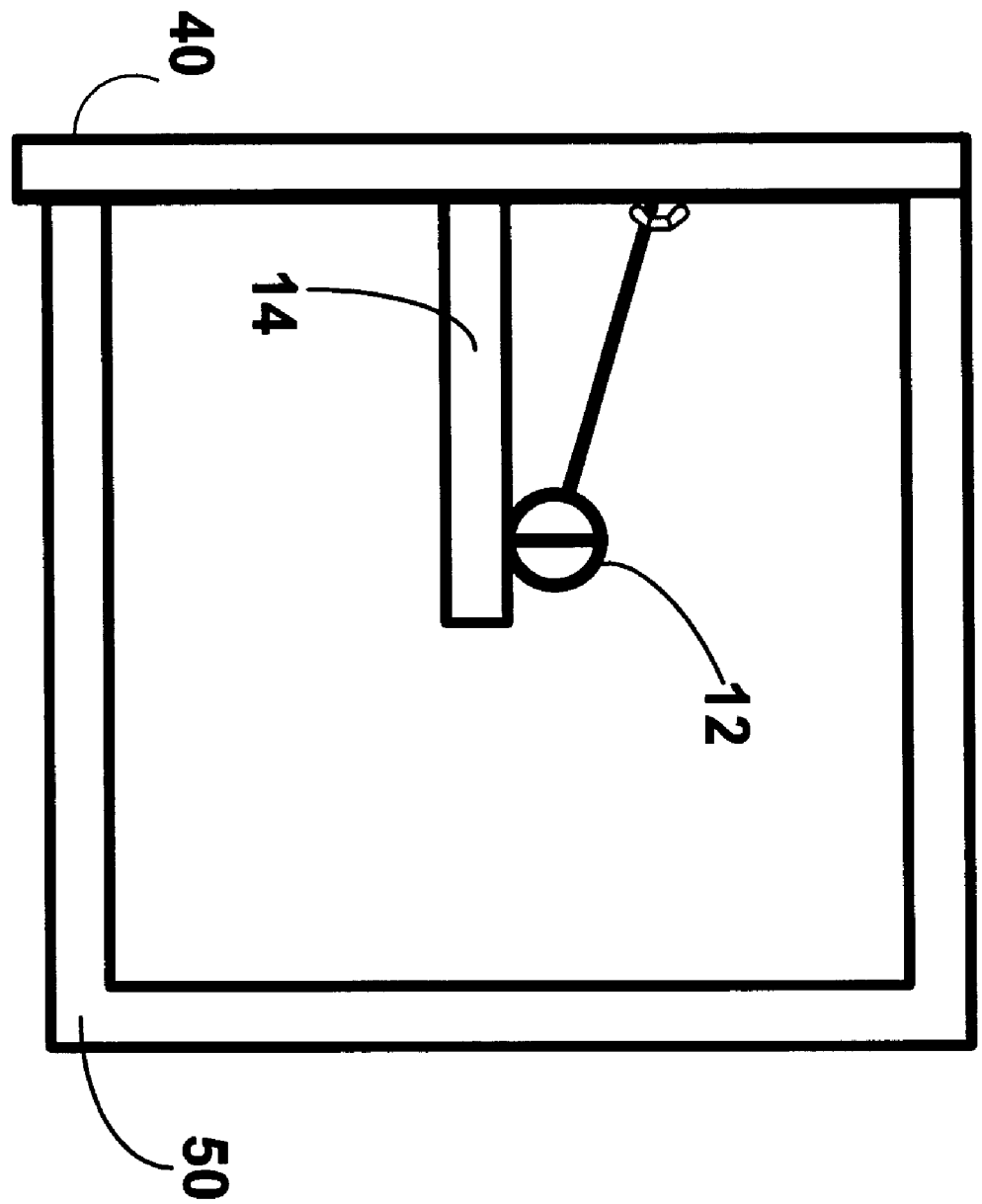

FIG. 4A-4B show an exemplary detector in the pill box of FIG. 3 to detect the pouring of pills from a compartment of the pill box. FIG. 4A shows a compartment 50 having a door 40 at a rest (not tilted) position. The electrode 14 is connected to the wire 13 to terminal B, while the pendulum 12 is connected to the wire 11 to terminal A. The pendulum 12 is swivably mounted on a hinge 15. FIG. 4B shows the pill box being tilted. As a result of the tilt, the pendulum 12 contacts the electrode 14 to complete the circuit and provide power to the control electronic 20. This approach turns on power only when necessary, and thus saves battery life and provides for a carefree operation where the patient needs not worry about battery replacement as the pill box can last for years. The pill box can be designed so that the battery can be replaced. Alternatively, the pill box can be disposable so that when the battery is depleted, a new pill box can be used to provide recurring revenue for the manufacturer.

FIG. 5 shows an exemplary method for dispensing one or more pills from the pill box. The method applies power to the control electronic 20 when the one or more pills are poured from the pill box (100). The control electronic 20 then identifies an opened compartment and an opening time (102). As discussed above, the switches 16 are used to determine the opening of one or more doors and a real-time clock chip can be used to determine the time of door opening. The control electronic 20 records the opened compartment and the opening time (104). The control electronic 20 also checks the opening time against one or more medication constraints and if so, generates an alarm if the medication constraint is violated (106). The medical constraints are typically set by the pharmaceutical company, by the FDA, or by the doctor. The constraints can be, for example, taking medication on a non-empty stomach or alternatively can be taking medication on an empty stomach. The control electronic 20 also checks for multiple compartment openings during one medication dispensing event and if so, generates an alarm (108). The control electronic 20 wirelessly transmits the recorded opened compartment and opening time to a computer (110) that can be the patient's home computer with a mesh network wireless communication device mounted therein to receive the data. The computer can store the data, or can upload the data to a central server over the Internet 30. The computer or the server can allow one or more authorized persons to review the medication dispensing (112) and can also request a medication refill (114).

FIG. 6 shows an exemplary method for dispensing pills/compliance monitoring and collecting patient data as well as providing educational information to the patient regarding the treatment using the pill box. The process optionally asks if the patient would like information about medication and if so display a summary of the medication, requirements prior to taking medication, and potential side effects or warnings (200). The information can be supplied by a pharmacist and downloaded or programmed into the pill box for display. Alternatively, the pill box can access a search engine and provide the information to the patient. Next, the system identifies an opened compartment and an opening time (202) and records the opened compartment and the opening time (204). The system checks the opening time against one or more medication constraints and if so, generates an alarm if the medication constraint is violated (206). The system can check for multiple compartment openings during one medication dispensing event and if so, generate an alarm (208). Optionally, the pill box can query other devices to collect information on patient (210). For example, the pill box can prompt the patient to obtain EKG and/or blood pressure from a suitable device that communicates over the mesh network. The data is collected and saved by the pill box electronic. The pillbox can also optionally display one or more predesigned questions about the user's health and collect answer(s) from the question(s) (212). Such questionnaires can include questions on the patient's general feeling and health assessment, questions on the patient's sugar level and blood pressure, questions about the type of food, the type of exercise, or any other questions that a healthcare plan, Medicare/Medicaid, employer health plan, or other suitable payors or physicians, nursing home directors, or family members may want the system to collect. The system then wirelessly transmits the recorded opened compartment(s) indicative of medication compliance and other collected patient data to a computer (214). The data is sent to a server and one or more authorized persons can, upon authentication, review the medication compliance information and collected patient data (216). The system can also requests a medication refill if needed (218).

In yet another embodiment, a pillbox is positioned on a scale or weight measurement device. The weight of each pill to be taken by a person is identified in advance, and the total weight of all pills to be taken in one batch, for example morning pills, is determined. When the pillbox is removed and placed back on the cradle, the new weight of the pillbox is determined. If the new weight is approximately equal to the old weight minus the total weight of pills to be taken in one patch, the system infers that the pills have been removed and (presumably) taken by the patient. If the new weight is not as expected, an error is indicated so that the patient, a caretaker, or the physician is notified of a potential drug non-compliance.

While the system above monitors the dispensing one or more pills from a pill box by applying power when the one or more pills are poured from the pill box; identifying an opened compartment and an opening time; and recording the opened compartment and the opening time, the system can also monitors the pill dispensing by applying power when the compartment door is opened and then detecting which door has been opened. Hence, the tilt detector (such as the pendulum) is not needed in all embodiments.

What is claimed is:

1. A method for dispensing one or more pills from a pill box, comprising:
   a. applying power when one or more pills are poured from the pill box;
   b. identifying an opened compartment and an opening time;
   c. moving a pendulum to an electrode to detect a pill box tilt condition; and
   d. recording the opened compartment and the opening time.

2. The method of claim 1, comprising checking the opening time against one or more medication constraints.

3. The method of claim 2, wherein the medical constraint comprises taking medication on one of: a full stomach, a non-empty stomach, an empty stomach.

4. The method of claim 2, comprising generating an alarm.

5. The method of claim 1, comprising checking for multiple compartment openings during one medication dispensing event.

6. The method of claim 5, comprising generating an alarm.

7. The method of claim 1, comprising wirelessly transmitting the recorded opened compartment and opening time to a computer.

8. The method of claim 1, comprising allowing one or more authorized persons to review the medication dispensing.

9. The method of claim 1, comprising requesting a medication refill.

10. A medication pill box, comprising:
    a. a processor to detect one or more compartment openings for a pill box;
    b. a power source; and
    c. a pill dispensing sensor coupled to the power source and the processor, the pill dispensing sensor applying power to the processor when one or more pills are poured from the pill box when a pendulum moves to an electrode to detect a pill box tilt condition, wherein the processor identifies and records an opened compartment and an opening time.

11. The pill box of claim 10, comprising one or more switches each coupled to a pill box compartment door to detect a compartment door opening.

12. The pill box of claim 11, wherein each switch comprises a first electrically conductive portion on the compartment door adapted to contact a second electrically conductive portion on a pill box wall adapted to contact the door.

13. The pill box of claim 10, comprising processor executable code to check a door opening time against one or more medication constraints.

14. The pill box of claim 13, wherein the medical constraint comprises taking medication on one of: a full stomach, a non-empty stomach and an empty stomach.

15. The pill box of claim 10, comprising processor executable code to check for multiple compartment openings during one medication dispensing event.

16. The pill box of claim 10, comprising a transmitter to send the recorded opened compartment and opening time to a computer.

17. The pill box of claim 16, wherein the computer allows one or more authorized persons to review the medication dispensing and wherein the computer requests a medication refill.

18. The pill box of claim 16, wherein the transmitter communicates with a mesh network.

19. The pill box of claim 10, wherein the pill dispensing sensor comprises one of: a door open switch, a door closed switch, a motion sensor, a pendulum, an accelerometer, a magnetic sensor.

* * * * *